US012044838B2

(12) United States Patent
Murayama et al.

(10) Patent No.: US 12,044,838 B2
(45) Date of Patent: Jul. 23, 2024

(54) LAMINATED LENS ARRAY, ENDOSCOPE AND IMAGE PICKUP UNIT

(71) Applicant: OLYMPUS CORPORATION, Tokyo (JP)

(72) Inventors: Masahiko Murayama, Hachioji (JP); Takuto Yoshinaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1050 days.

(21) Appl. No.: 16/923,354

(22) Filed: Jul. 8, 2020

(65) Prior Publication Data

US 2020/0341263 A1   Oct. 29, 2020

Related U.S. Application Data

(63) Continuation of application No. PCT/JP2018/039110, filed on Oct. 19, 2018.

(30) Foreign Application Priority Data

Jan. 9, 2018  (JP) .................................. 2018-001362

(51) Int. Cl.
*G02B 13/00* (2006.01)
*A61B 1/00* (2006.01)
(Continued)

(52) U.S. Cl.
CPC ........ *G02B 23/243* (2013.01); *A61B 1/00197* (2013.01); *A61B 1/05* (2013.01);
(Continued)

(58) Field of Classification Search
CPC .............. G02B 13/0015; G02B 13/006; G02B 3/0012; G02B 3/0025; G02B 3/0037;
(Continued)

(56) References Cited

U.S. PATENT DOCUMENTS 5,871,440 A   2/1999  Okada
6,905,462 B1  6/2005  Homma et al.
(Continued)

FOREIGN PATENT DOCUMENTS

CN        101170941 A    4/2008
EP          1211543 A1    6/2002
(Continued)

OTHER PUBLICATIONS

International Search Report dated Jan. 22, 2019 issued in PCT/JP2018/039110.

*Primary Examiner* — Wyatt A Stoffa
*Assistant Examiner* — Samanvitha Sridhar
(74) *Attorney, Agent, or Firm* — Scully, Scott, Murphy & Presser, P.C.

(57) ABSTRACT

There is provided a laminated lens array in which a first lens element arranged on a distal end side and a second lens element arranged on a proximal end side are stuck and laminated in a lamination direction, wherein outer faces of a laminated body including the first lens element and the second lens element are located in the lamination direction and have concaves formed being recessed toward a center of the laminated body at least on parts of the outer faces in the lamination direction.

14 Claims, 7 Drawing Sheets

(51) Int. Cl.
*A61B 1/05* (2006.01)
*G02B 3/00* (2006.01)
*G02B 23/24* (2006.01)
*A61B 1/018* (2006.01)
*A61B 18/00* (2006.01)
*A61B 18/20* (2006.01)

(52) U.S. Cl.
CPC ......... *G02B 3/0075* (2013.01); *G02B 13/006* (2013.01); *A61B 1/018* (2013.01); *A61B 2018/00595* (2013.01); *A61B 18/201* (2013.01); *G02B 23/2469* (2013.01)

(58) Field of Classification Search
CPC .. G02B 3/0056; G02B 3/0062; G02B 3/0068; G02B 3/0075; G02B 3/02; G02B 3/08; G02B 23/24; G02B 2003/0093; G02B 5/1814; G02B 7/02; G02B 6/0036; A61B 1/00096; A61B 1/0011; A61B 1/05; H04N 23/27
USPC .......................................................... 359/741
See application file for complete search history.

(56) References Cited

U.S. PATENT DOCUMENTS

| | | | | |
|---|---|---|---|---|
| 2006/0158748 | A1* | 7/2006 | Hirata | G02B 27/62 359/811 |
| 2008/0055748 | A1* | 3/2008 | Konno | G02B 23/243 359/811 |
| 2009/0253966 | A1 | 10/2009 | Ichimura | |
| 2010/0085466 | A1* | 4/2010 | Fujimori | H01L 27/14687 348/340 |
| 2016/0295085 | A1* | 10/2016 | Aoyama | A61B 1/00188 |
| 2017/0059848 | A1* | 3/2017 | Haraguchi | G02B 23/2469 |
| 2017/0307872 | A1* | 10/2017 | Hatase | H04N 23/51 |
| 2017/0336625 | A1 | 11/2017 | Amanai et al. | |

FOREIGN PATENT DOCUMENTS

| | | | | |
|---|---|---|---|---|
| EP | 1880656 | A1 | 1/2008 | |
| JP | S63-106617 | A | 5/1988 | |
| JP | H06-233738 | A | 8/1994 | |
| JP | H08-545 | A | 1/1996 | |
| JP | H09-220192 | A | 8/1997 | |
| JP | H09220192 | A * | 8/1997 | ............... A61B 1/00 |
| JP | 2004-032190 | A | 1/2004 | |
| JP | 2004029554 | A * | 1/2004 | ......... G02B 13/0085 |
| JP | 2006-314459 | A | 11/2006 | |
| JP | 2015080646 | A * | 4/2015 | |
| JP | 2017-030252 | A | 2/2017 | |
| JP | 2017-195960 | A | 11/2017 | |
| JP | 2017-207658 | A | 11/2017 | |
| WO | WO 01/018585 | A1 | 3/2001 | |
| WO | WO 2006/120797 | A1 | 11/2006 | |
| WO | WO-2017168959 | A1 * | 10/2017 | ............... G02B 7/02 |
| WO | WO-2017169644 | A1 * | 10/2017 | ............. G02B 7/021 |

\* cited by examiner

R10<R12

R12>R10

LAMINATED LENS ARRAY, ENDOSCOPE AND IMAGE PICKUP UNIT

CROSS REFERENCE TO RELATED APPLICATION

This application is a continuation application of PCT/JP2018/039110 filed on Oct. 19, 2018 and claims benefit of Japanese Application No. 2018-001362 filed in Japan on Jan. 9, 2018, the entire contents of which are incorporated herein by this reference.

BACKGROUND OF THE INVENTION

1. Field of the Invention

The present invention relates to a laminated lens array in which a first lens element arranged on one side and a second lens element arranged on the other side opposite to the one side are laminated in a lamination direction connecting the one side and the other side, an endoscope and an image pickup unit.

2. Description of the Related Art

Recently, endoscopes have been widely used in a medical field and an industrial field. An endoscope used in the medical field and the industrial field makes it possible to, by inserting the elongated insertion portion into a subject/object, observe an inside of the subject/object located more toward one side than an image pickup unit provided in a distal end portion of the insertion portion, by the image pickup unit.

The image pickup unit is fitted and arranged in a hole formed in a distal end rigid member constituting the distal end portion and is provided with an objective lens unit.

The objective lens unit is provided with an objective lens, which is a first lens element exposed on a distal end face of the distal end portion of the insertion portion, and an optical lens, which is one or more second lens elements located behind the objective lens.

Further, the image pickup unit is provided with an image pickup device, such as a CCD or a CMOS, arranged on the other side opposite to the one side relative to the second lens element and configured to pick up an image of the inside of the subject/object via the objective lens unit, a substrate electrically connected to the image pickup device and implemented with electronic parts, and cables and the like electrically connected to the substrate and configured to give and receive electrical signals to and from the substrate.

Furthermore, in the insertion portion, other internal components such as a light guide fiber bundle configured to supply illumination light into the subject/object and an already known treatment instrument insertion channel are arranged in addition to the image pickup unit described above.

One side of the light guide fiber bundle and one side of a treatment instrument insertion channel are arranged in holes formed in the distal end rigid member, which are different from the hole in which the image pickup unit is formed, respectively. A light emitting end portion of the light guide fiber bundle and an opening of the treatment instrument insertion channel are fixed to be exposed on the distal end face of the distal end portion.

Here, a configuration is well known in which a rigid length of the distal end rigid member of the distal end portion in the direction connecting the one side and the other side described above is shortened, and, for the purpose of reducing a diameter, a laminated lens array in which a plurality of lens elements are stuck so as to be laminated in the direction connecting the one side and the other side described above is used for the objective lens unit, and the configuration is disclosed in Japanese Patent Application Laid-Open Publication No. 2017-30252.

In Japanese Patent Application Laid-Open Publication No. 2017-30252, a method for manufacturing a plurality of laminated lens arrays, an external shape of each of the laminated lens arrays, that is, a shape of outer faces being formed in a rectangular shape, by sticking a plurality of large plates and then cutting the large plates by dicing, and a configuration of the laminated lens array are disclosed.

SUMMARY OF THE INVENTION

A laminated lens array according to one aspect of the present invention is a laminated lens array in which a first lens element arranged on one side and a second lens element arranged on another side opposite to the one side are stuck and laminated in a lamination direction connecting the one side and the other side, wherein outer faces of a laminated body including the first lens element and the second lens element are located in the lamination direction and have concaves formed being recessed toward a center of the laminated body at least on parts of the outer faces in the lamination direction.

An endoscope according to one aspect of the present invention is an endoscope including the laminated lens array having the concaves, in a distal end portion of an insertion portion, wherein other internal components in the distal end portion are arranged along outer circumferences of the concaves.

Furthermore, an image pickup unit according to one aspect of the present invention includes: the laminated lens array; and an image pickup device on which light transmitted through the laminated lens array is incident.

DETAILED DESCRIPTION OF PREFERRED EMBODIMENTS

Embodiments of the present invention will be described below with reference to drawings. Note that it should be noticed that the drawings are schematic, and a relationship between thickness and width of each member, a thickness ratio among respective members and the like are different from actual ones, and it goes without saying that, among the drawings, portions having a different mutual dimensional relationship or ratio are included.

First Embodiment

Figure 1:
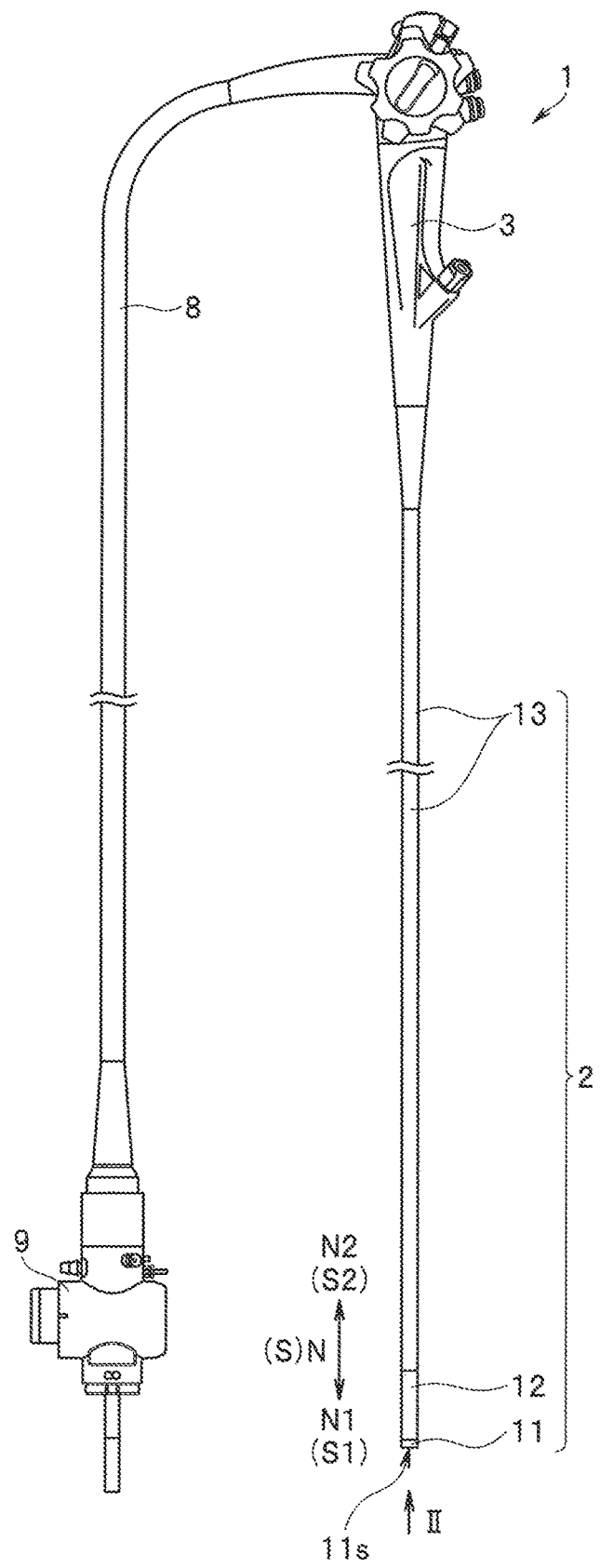
FIG. 1 is a diagram showing an endoscope provided with a laminated lens array of a first embodiment in a distal end portion of an insertion portion.

FIG. 1 is a diagram showing an endoscope provided with a laminated lens array of the present embodiment in a distal end portion of an insertion portion.

As shown in FIG. 1, a main part of an endoscope 1 is configured, being provided with an insertion portion 2 to be inserted into a subject/object, an operation portion 3 connectedly provided on a proximal end side N2 of the insertion portion 2 in an insertion direction N, a universal cord 8 extended from the operation portion 3, and a connector 9 provided on an extension end of the universal cord 8.

Note that the endoscope 1 is electrically connected to external apparatuses such as a control apparatus and an illumination apparatus via the connector 9.

The insertion portion 2 is configured, being provided with a distal end portion 11, a bending portion 12 and a flexible tube portion 13 in that order from a distal end side N1 in the insertion direction N and is elongatedly formed.

By being bent, for example, in four directions of upward, downward, left and right directions accompanying a bending operation, the bending portion 12 changes an observation direction of an objective lens unit in an image pickup unit provided in the distal end portion 11 and causes insertability of the distal end portion 11 in a subject/object to be improved, the image pickup unit not being shown. Furthermore, the flexible tube portion 13 is connectedly provided on the proximal end side N2 of the bending portion 12.

Next, description will be made on a configuration of a laminated lens array constituting the objective lens unit in the image pickup unit provided in the distal end portion 11, using FIGS. 2 to 4.

Note that, in the embodiment shown below, only the laminated lens array of the objective lens unit will be shown for simplification of drawings.

Figure 2:
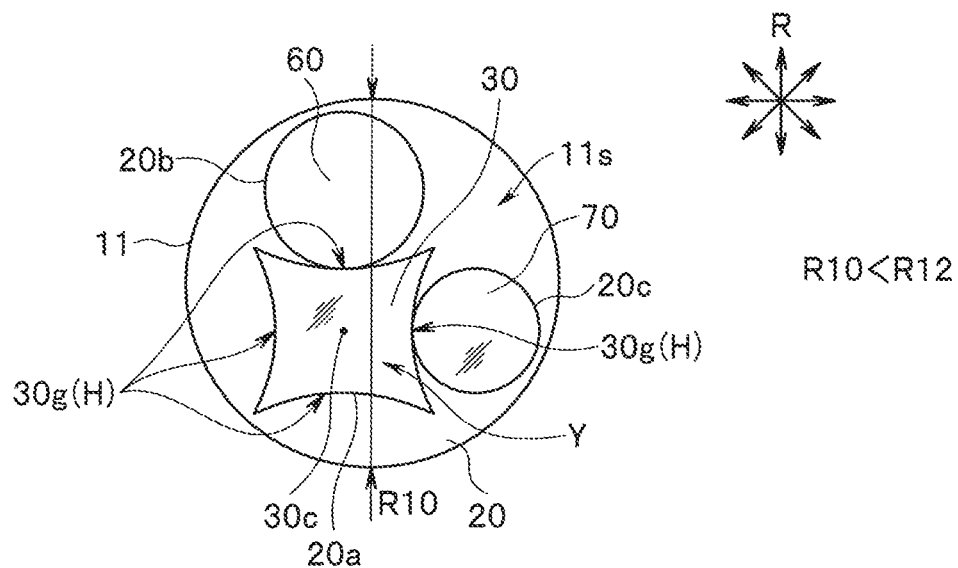
FIG. 2 is a from view in which a distal end face of the insertion portion of FIG. 1 is seen in a direction II in FIG. 1.

FIG. 2 is a front view in which a distal end face of the insertion portion of FIG. 1 is seen in a direction II in FIG. 1; FIG. 3 is a front view showing a distal end face of an insertion portion of a conventional endoscope; and FIG. 4 is a side view of the laminated lens array of FIG. 2.

As shown in FIG. 2, the distal end portion 11 has a substantially circular outer shape, and is provided with a distal end rigid member 20 elongated in the insertion direction N and configured, for example, with resin or metal.

In the distal end rigid member 20, a plurality of, for example, three through holes 20a to 20c are formed in the insertion direction N.

Note that the number of through holes is not limited to three. Further, all the through holes 20a to 20c may be connected in an outer diameter direction R.

Figure 4:
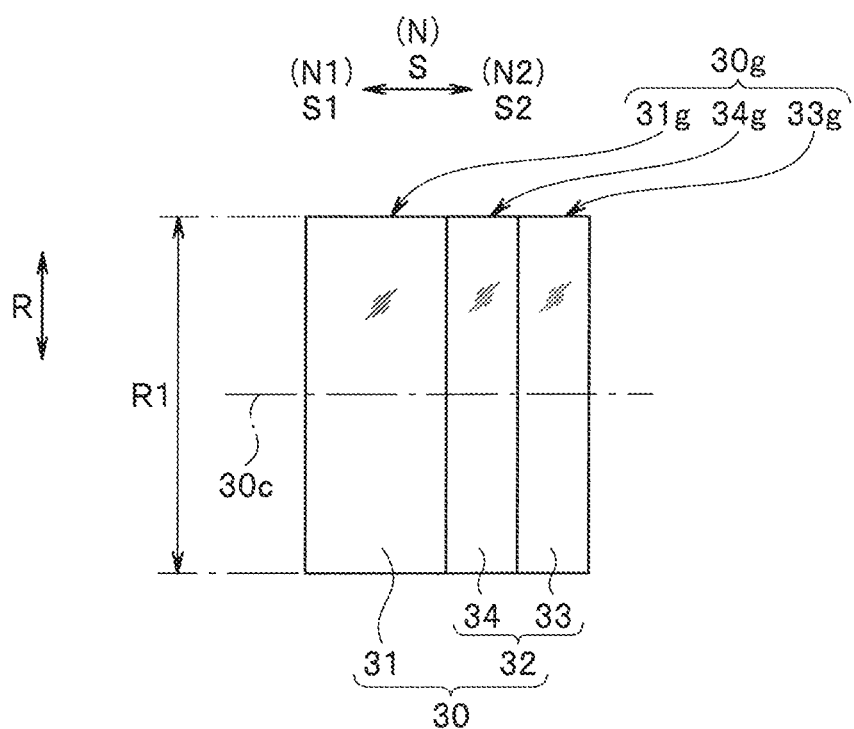
FIG. 4 is a side view of the laminated lens array of FIG. 2.

A laminated lens array 30, which is a laminated body shown in FIG. 4, is fitted in the through hole 20a, and an objective lens 31, which is a first lens element, is fixed to be exposed on a distal end face 11s.

The distal end side N1 of a treatment instrument insertion channel 60, which is another internal component, is fixed in the through hole 20b, and a distal end of the treatment instrument insertion channel 60 is opened on the distal end face 11s.

Furthermore, the distal end sides N1 of an illumination lens 70 and a light guide not shown, which are other internal components, are fitted and fixed in the through hole 20c, and the illumination lens 70 is fixed to be exposed on the distal end face 11s.

As shown in FIG. 4, in the laminated lens array 30, the objective lens 31 arranged on a distal end side S1, which is one side corresponding to the distal end side N1 in the insertion direction N, and a second lens element 32 arranged on a proximal end side S2, which is the other side that is the opposite side of the distal end side S1 and is the other side corresponding to the proximal end side N2 in the insertion direction N are laminated by being stuck by adhesive or the like in such a manner that external shapes correspond to each other in a lamination direction S connecting the distal end side S1 and the proximal end side S2 and corresponding to the insertion direction N.

The second lens element 32 is configured with a plurality of, for example, two lens elements. A lens 33, which is a third lens element located on the most proximal end side S2, and a lens 34, which is a fourth lens element sandwiched between the objective lens 31 and the lens 33 in the lamination direction S, are stuck by adhesive or the like such that external shapes correspond to each other and laminated in the lamination direction S.

Note that though the case where the second lens element 32 is configured with two lens elements is shown as an example in the present embodiment, the second lens element 32 may be, of course, configured with three or more lens elements. In other words, the fourth lens element may be configured with a plurality of lens elements.

Further, when the laminated lens array 30 is arranged in the distal end portion 11, an image pickup device 50 constituting the image pickup unit on which light condensed by the laminated lens array 30 is caused to be incident is provided in the distal end portion 11 on the proximal end side S2 with respect to the lens 33, which will be shown in FIG. 8 described later.

Further, in the present embodiment, the laminated lens array 30, that is, the objective lens 31, the lens 33 and the lens 34 are formed in shapes having the same outer diameter and the same cross-sectional area in the outer diameter direction R.

More specifically, as shown in FIGS. 2 and 4, four outer faces 30g of the laminated lens array 30 are located in the lamination direction S, and each outer face 30g is formed in a shape having a concave part H, which is a concave recessed toward a center 30c of the laminated lens array 30, on a part of the outer face 30g in the lamination direction S.

More specifically, an external shape of each of four outer faces 31g of the objective lens 31, four outer faces 33g of the lens 33 and four outer faces 34g of the lens 34 is formed in a shape semicircularly recessed toward the center 30c from a rectangular shape, that is, a shape having the concave part H.

Therefore, the external shape of the laminated lens array 30 is such a shape that only at least an effective field-of-view area Y, through which light incident on the image pickup device 50 in the laminated lens array 30 passes, except adhesive margins among the lenses 31, 34 and 33 is left.

Note that a shape of the effective field-of-view area Y is not limited to the shape shown in FIGS. 2 and 4, and any shape with the concave parts H formed on the outer faces 30g is possible.

Figure 3:
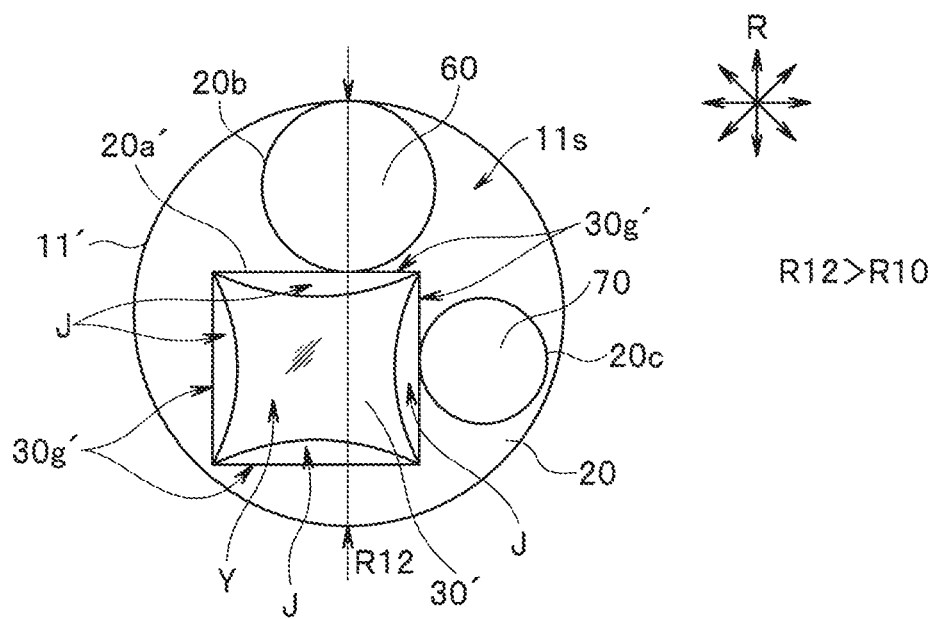
FIG. 3 is a front view showing a distal end face of an insertion portion of a conventional endoscope.

In other words, the external shape of the laminated lens array 30 of the present embodiment is different from a conventional laminated lens array 30' the external shape of which is formed in a rectangular shape without the concave parts H being formed on four outer faces 30g' shown in FIG. 3.

More specifically, in the conventional laminated lens array 30', dead spaces J, which are not the effective field-of-view area Y, are formed between the effective field-of-view area V and the outer faces 30g'. However, the laminated lens array 30 of the present embodiment is formed in an external shape that does not have the dead spaces J. Therefore, the concave parts H are formed outside the effective field-of-view area Y.

The concave parts H may be formed at the time of integrally molding the laminated lens array 30 or may be formed by, after sticking and integrating the objective lens 31, the lens 34 and the lens 33, shaving the outer faces 30g by post-processing.

Note that since other components of the laminated lens array 30 are the same as components of the conventional laminated lens array 30', description of the components will be omitted.

Thus, in the present embodiment, it has been shown that, on the objective lens 31 and the lenses 33 and 34 constituting the laminated lens array 30, the external shape of each of the four outer faces 31g of the objective lens 31, the four outer faces 33g of the lens 33 and the four outer faces 34g of the lens 34 is formed in a shape semicircularly recessed toward the center 30c from a rectangular shape, that is, a shape having the concave part H.

In other words, it has been shown that the external shape of the laminated lens array 30 is formed in such a shape that almost only the effective field-of-view area Y of the laminated lens array 30 except the adhesive margins among the lenses 31, 34 and 33 is left.

According to the above, it is possible to cause a cross-sectional area of the laminated lens array 30 in the outer diameter direction R to be reduced in comparison with the conventional laminated lens array 30' by an amount corresponding to the dead spaces J, that is, by an amount corresponding to the concave parts H without causing the effective field-of-view area Y to be reduced, as shown in FIGS. 2 and 3.

Therefore, as shown in FIGS. 2 and 3, the treatment instrument insertion channel 60, the illumination lens 70 and light guide fibers (not shown) configured to supply illumination light to the illumination lens 70, which are other internal components arranged in the distal end rigid member 20 of the distal end portion 11, can be arranged closer to the laminated lens array 30 by the amount corresponding to the dead spaces J in the outer diameter direction R of the distal end portion 11 than a conventional distal end portion 11', that is, can be arranged along the concave parts H.

Note that the above also applies to a case where an illumination chip 71, such as an LED, described later (see FIG. 8) is arranged on the distal end portion 11 instead of the light guide fibers, and the illumination chip 71 can also be arranged close to the laminated lens array 30 by the amount corresponding to the dead spaces J along the concave parts H.

Therefore, in comparison with the conventional configuration, it is possible to make an outer diameter R10 of the distal end portion 11 smaller than an outer diameter R12 of the conventional distal end portion 11' (R10<R12) without reducing diameters of the treatment instrument insertion channel 60 and the illumination lens 70, that is, while securing functions such as brightness of illumination light and a channel diameter similar to conventional functions.

From the above, it is possible to provide the laminated lens array 30 provided with a configuration capable of reducing the cross-sectional area in the outer diameter direction R without reducing the effective field-of-view area Y, and the endoscope 1.

Figure 5:
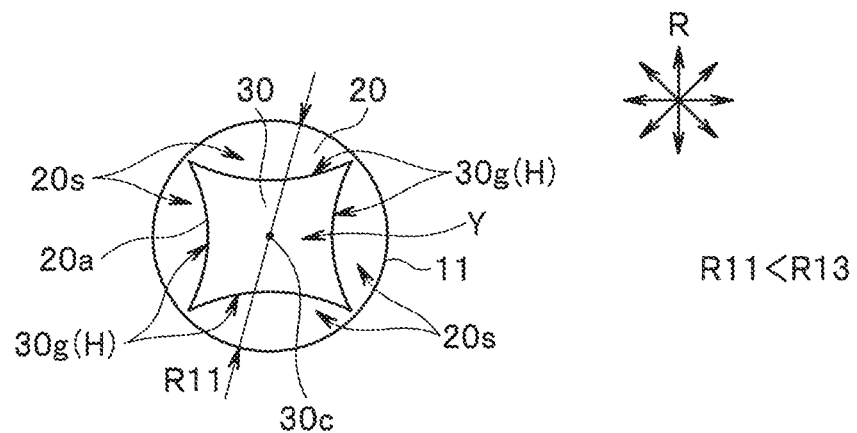
FIG. 5 is a front view of a distal end thee of a distal end portion that does not have a treatment instrument insertion channel.

Note that a modification will be shown below using FIGS. 5 and 6. FIG. 5 is a front view of a distal end face of a distal end portion that does not have a treatment instrument insertion channel; and FIG. 6 is a front view of a distal end face of a conventional distal end portion that does not have a treatment instrument insertion channel.

In the present embodiment described above, the case where the treatment instrument insertion channel 60 is provided in the distal end rigid member 20 in addition to the laminated lens array 30 and the illumination lens 70 has been shown as an example. Regardless of the above, the present invention is also applicable to a configuration in which the treatment instrument insertion channel 60 is not provided as shown in FIG. 5.

In other words, in the present modification also, the external shape of each of the four outer faces 31g of the objective lens 31, the four outer faces 33g of the lens 33 and the four outer faces 34g of the lens 34 is also formed in a shape semicurcularly recessed toward the center 30c from a rectangular shape, that is, a shape having the concave part H as shown in FIG. 5.

Figure 6:
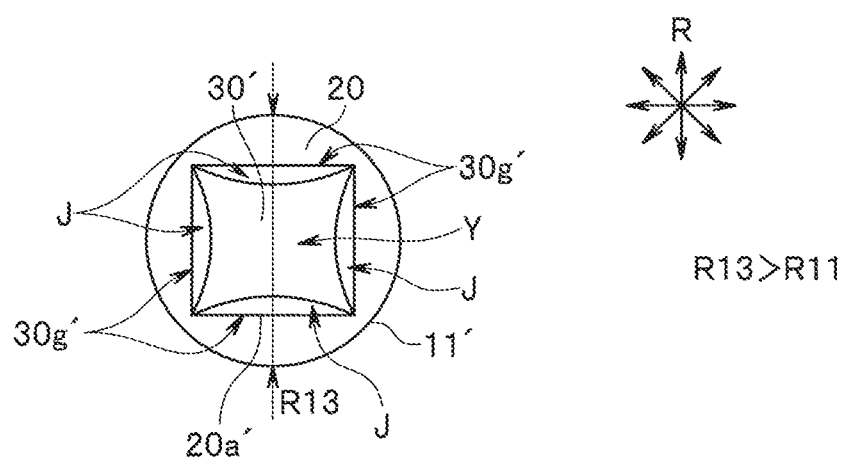
FIG. 6 is a front view of a distal end face of a conventional distal end portion that does not have a treatment instrument insertion channel.

Therefore, the external shape of the laminated lens array 30 of the present embodiment is different from a conventional laminated lens array 30' the external shape of which is formed in a rectangular shape without the concave parts H being formed on the four outer faces 30g' shown in FIG. 6.

More specifically, in the conventional laminated lens array 30', the dead spaces J are formed between the effective field-of-view area V and the outer faces 30g', but the laminated lens array 30 of the present embodiment is formed in an external shape that does not have the dead spaces J.

In this case, the illumination lens 70 can be arranged in any of spaces 20s between an outer circumference of the distal end portion 11 and the outer faces 30g of the laminated lens array 30 in the distal end rigid member 20. Note that other components are the same as the present embodiment described above.

Further, the above is applicable to a configuration not using the illumination lens 70, more specifically, a configuration in which tight guide fiber distal ends not shown are extended to the distal end face 11s to directly supply illumination to an inside of a subject/object from extension ends.

In this case, the light guide fibers in the distal end portion 11 can be arranged in any of the spaces 20s between the outer circumference of the distal end portion 11 and the outer faces 30g of the laminated lens array 30.

According to such a configuration, it is possible to, by the concave parts H formed on the outer faces 30g, make an outer diameter R11 of the distal end portion 11 smaller than an outer diameter R13 of the conventional distal end portion 11 shown in FIG. 6 (R11<R13) by the amount corresponding to the dead spaces J, that is, by the amount corresponding to the concave parts H. Note that other effects are the same as in the present embodiment described above.

Second Embodiment

Figure 7:
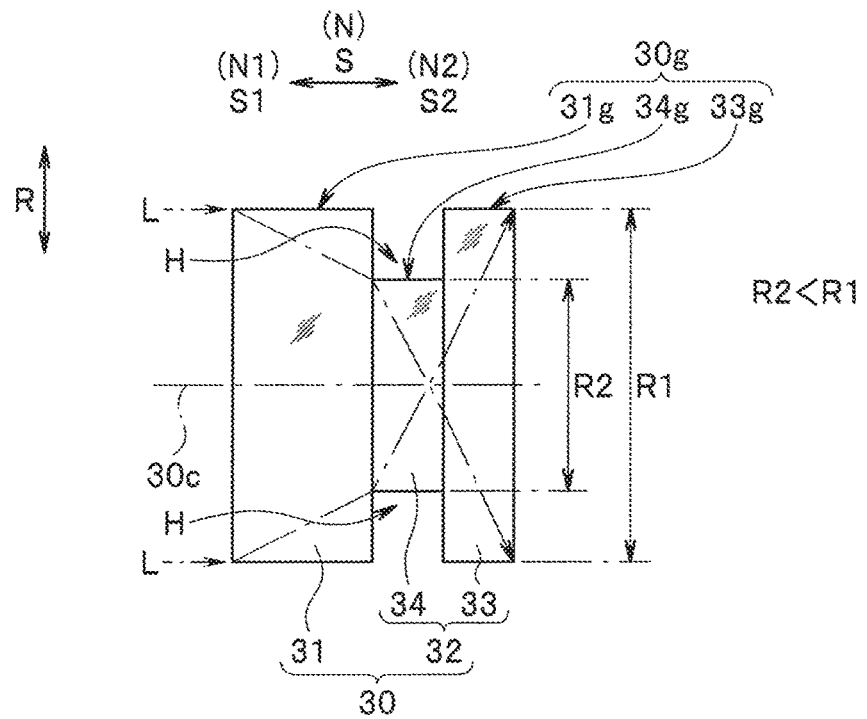
FIG. 7 is a side view of a laminated lens array of a second embodiment.
Figure 8:
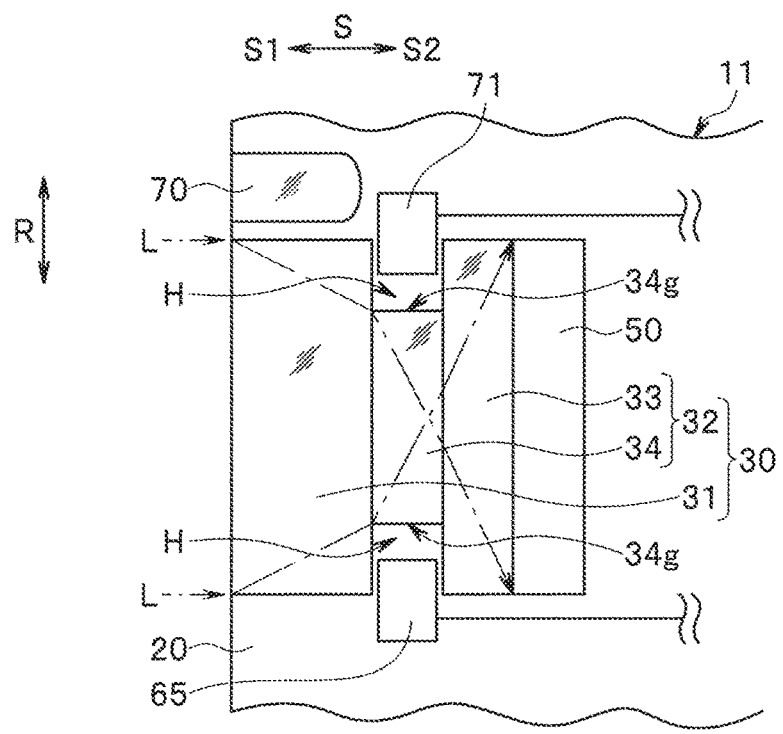
FIG. 8 is a diagram schematically showing a configuration in which the laminated lens array of FIG. 7 is provided in a distal end portion.

FIG. 7 is a side view of a laminated lens array of the present embodiment; and FIG. 8 is a diagram schematically showing a configuration in which the laminated lens array of FIG. 7 is provided in a distal end portion.

In comparison with the laminated lens array of the first embodiment shown in FIGS. 1 to 6 described above, a configuration of the laminated lens array of the second embodiment is different in a point that the outer faces of the fourth lens element are located more toward a center side than the outer faces of the first and third lens elements and a point that the external shape of the laminated lens array is formed in a rectangular shape. Therefore, only the different points will be described. Components similar to components of the first embodiment will be given the same reference numerals, and description of the components will be omitted.

Note that, in the present embodiment also, only the laminated lens array of the objective lens unit will be shown for simplification of drawings. Further, the case where the second lens element is configured with two lens elements will be shown as an example.

In the present embodiment also, the four outer faces 30g of the laminated lens array 30 are located in the lamination direction S, and each outer face 30g is formed in a shape having the concave part H recessed toward the center 30c of the laminated lens array 30, on a part of the outer face 30g in the lamination direction S.

More specifically, in the present embodiment, the outer shapes of the objective lens 31 and the lenses 33 and 34 are formed in rectangular shapes. Further, as shown in FIG. 7, the outer faces 31g and 33g of the objective lens 31 and the lens 33 are formed to have the same outer diameter R1 in the outer diameter direction R and formed to have the same cross-sectional area.

Further, as shown in FIG. 7, the outer faces 34g of the lens 34 are located more toward the center 30c side of the laminated lens array 30 than the outer faces 31g of the objective lens 31 and the outer faces 33g of the lens 33 in the outer diameter direction R. Thereby, concave parts H are formed on a part of the outer faces 30g.

In other words, an outer diameter R2 of the outer face 34g of the lens 34 is formed smaller than the outer diameter R1 of the outer face 31g of the objective lens 31 and the outer face 33g of the lens 33 (R2<R1).

Note that even though the outer diameter R2 of the lens 34 is formed smaller than the outer diameter R1 of the objective lens 31 and the lens 33, the effective field-of-view area Y of the lens 34 does not decrease.

This is because, due to optical characteristics of the laminated lens array 30 configured with the three lens elements 31, 34 and 33, a range of a light beam L that passes through the lens 34 sandwiched between the objective lens 31 and the lens 33 in the lamination direction S is closer to the center 30c than the objective lens 31 and the lens 33.

In other words, the lens 34 is formed to have the outer diameter R2 by the outer faces 34g other than the range through which the light beam L passes being shrink-molded or processed.

Note that other components of the laminated lens array 30 are the same as components of the laminated lens array 30 of the first embodiment.

According to such a configuration, it becomes possible to, when the laminated lens array 30 is arranged in the distal end rigid member 20 of the distal end portion 11, arrange a temperature sensor 65, the illumination chip 71 configured to supply illumination light to the illumination lens 70 and the like, which are other internal components, along a space formed by the concave parts H as shown in FIG. 8.

Therefore, since the temperature sensor 65 and the illumination chip 71 can be arranged on the center C side in the outer diameter direction R by an amount corresponding to the concave parts H, the diameter of the distal end portion 11 can be reduced by an amount corresponding thereto.

From the above, effects similar to the effects of the first embodiment described above can also be obtained by such a configuration.

Note that, in the present embodiment described above, it has been shown that the external shapes of the outer faces 31g of the objective lens 31 and the outer faces 33g of the lens 33 are formed in rectangular shapes.

Of course, regardless of the above, it does not matter if each of the four outer faces 31g and the four outer faces 33g is formed in a shape with the concave part H being formed similarly to the first embodiment described above.

Figure 9:
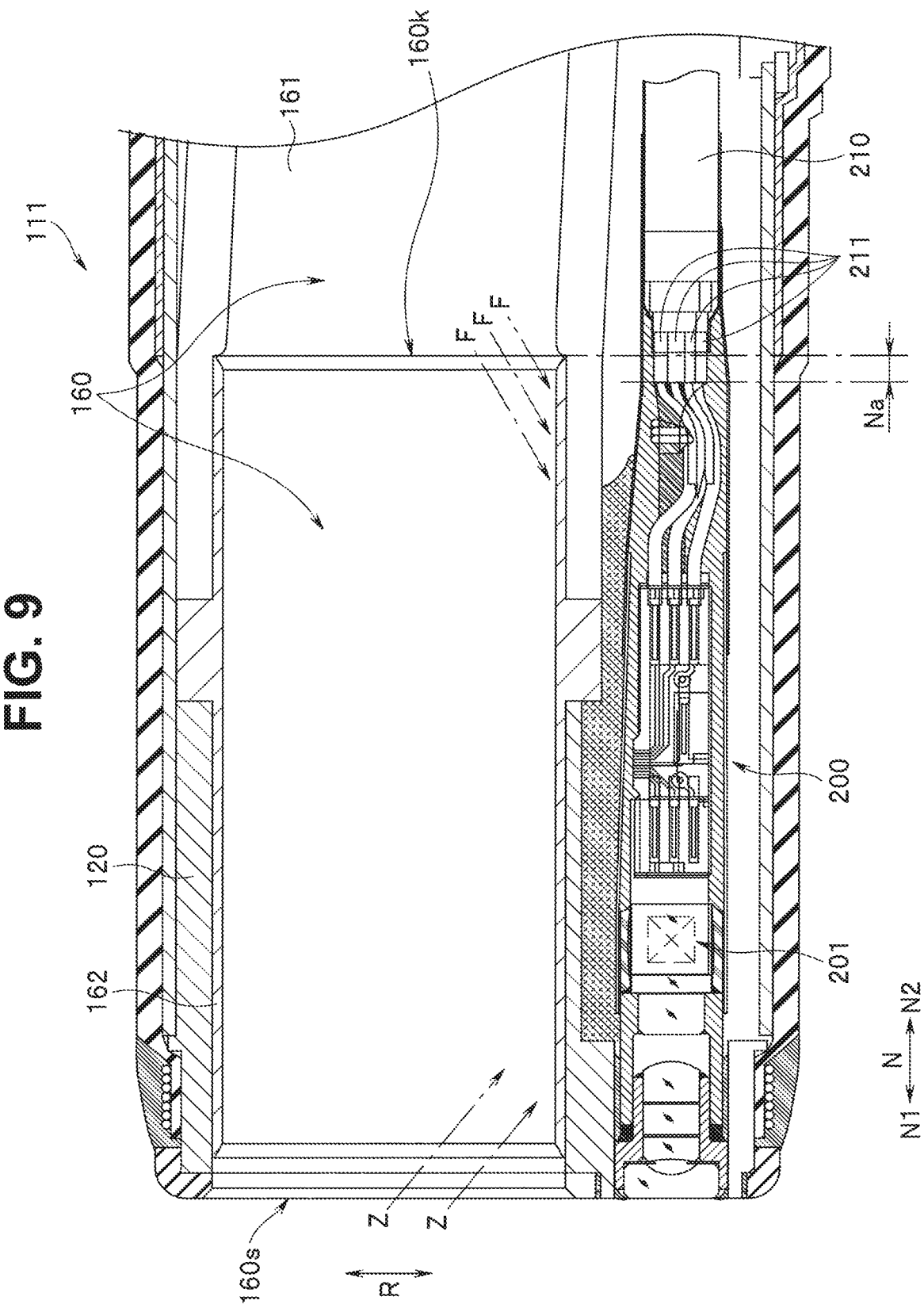
FIG. 9 is a partial sectional view of a distal end portion of an insertion portion of an endoscope.

As another configuration to reduce the diameter of the distal end portion 11 of the insertion portion 2 of the endoscope 1, a configuration shown in FIG. 9 is conceivable. FIG. 9 is a partial sectional view of a distal end portion of an insertion portion of an endoscope.

Conventionally, in a well-known endoscope, a treatment instrument insertion channel 160 formed in an insertion portion is configured by a distal end of a channel tube 161 being fixed to a proximal end of a rigid channel pipe sleeve 162 fitted in a distal end rigid member 120 of a distal end portion 111.

However, in the conventional configuration, there is a possibility that, at the time of causing a treatment instrument to be inserted into the treatment instrument insertion channel 160, a load F is given to an image pickup unit 200 arranged in the distal end rigid member 120 via the channel tube 161.

Further, in a case where the treatment instrument is a laser cautery apparatus, when laser cautery treatment is performed for a site to be examined, reflected light Z enters the image pickup unit 200 via a distal end opening 160s of the treatment instrument insertion channel 160 on a distal end face, and there is a possibility of causing known halation to occur.

Therefore, in the configuration shown in FIG. 9, the proximal end 160k of the channel pipe sleeve 162 is arranged on the proximal end side N2 behind a distal end of a cable strip 211 of a signal cable 210 electrically connected to a substrate in the image pickup unit 200 by Na.

According to the configuration, it is possible to reduce the load F given to the distal end side N1 of the cable strip 211 in the image pickup unit 200 from a treatment instrument that passes through the treatment instrument insertion channel 160 by the rigid channel pipe sleeve 162.

Further, since the proximal end 160k is located more toward the proximal end side N2 than a light receiving portion 201 of an image pickup device in the image pickup unit 200, it is possible to prevent the laser reflected light Z from entering the image pickup unit 200 by the channel pipe sleeve 162.

Therefore, since it becomes unnecessary to separately provide a frame or the like for shading on an outer circumference of the image pickup unit 200, it is possible to reduce the diameter of the distal end portion 111.

Figure 10:
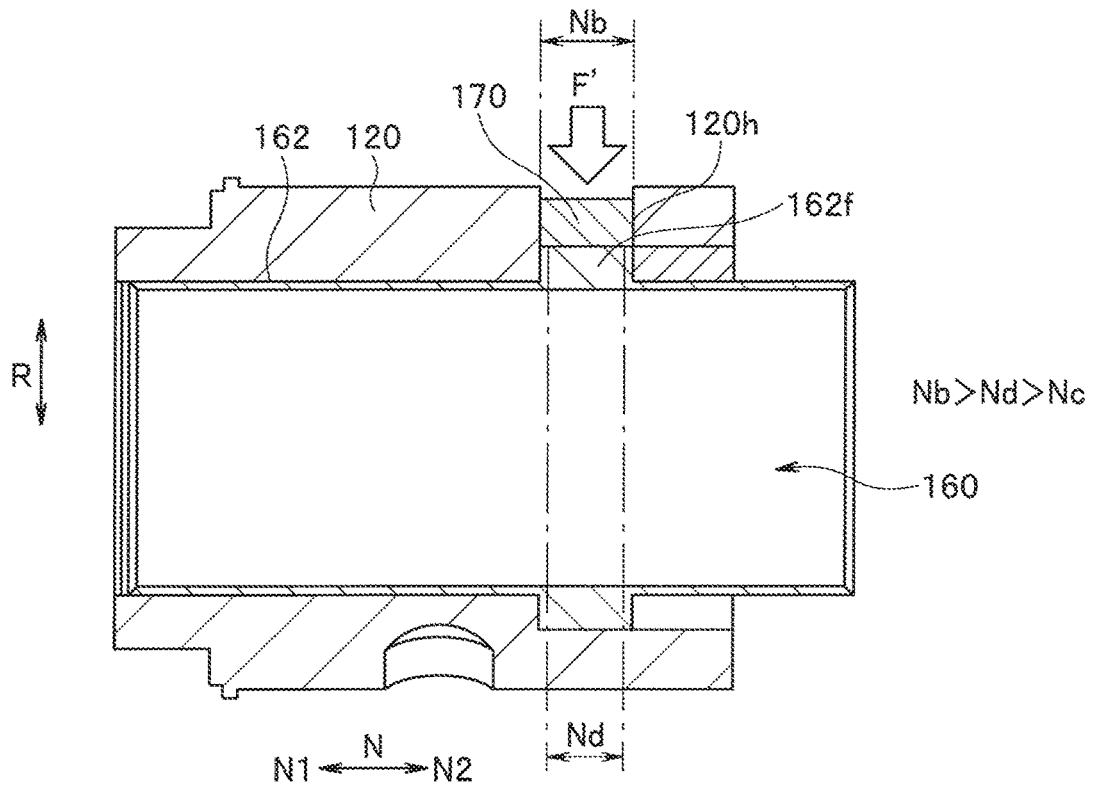
FIG. 10 is a partial sectional view showing a channel pipe sleeve provided on the distal end rigid member of the distal end portion of the insertion portion of the endoscope together with the distal end rigid member.

Further, as a configuration for fixing the channel pipe sleeve to the distal end rigid member, a configuration shown in FIG. 10 is conceivable.

Figure 11:
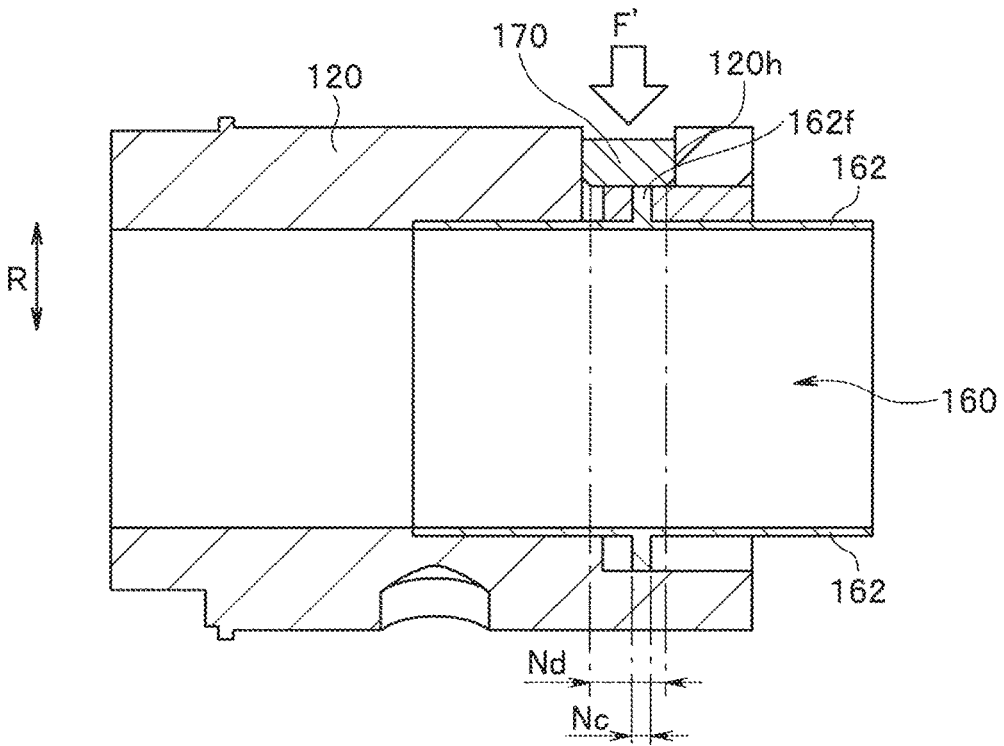
FIG. 11 is a partial sectional view showing a conventional channel pipe sleeve together with a distal end rigid member.

FIG. 10 is a partial sectional view showing a channel pipe sleeve provided on the distal end rigid member of the distal end portion of the insertion portion of the endoscope together with the distal end rigid member; and FIG. 11 is a partial sectional view showing a conventional channel pipe sleeve together with a distal end rigid member.

Conventionally, in a well-known endoscope, a configuration is used in which a screw 170 is caused to be screwed with a screw hole 120h from an outer side of the distal end rigid member 120 in the outer diameter direction R, and a distal end of the screw 170 is caused to be in contact with a flange 162f fitted in the screw hole 120h on an outer circumferential surface of the channel pipe sleeve 162, as a configuration for securing electrical continuity between the channel pipe sleeve 162 and the distal end rigid member 120, as shown in FIG. 11.

In the configuration, however, continuity cannot be secured if tightening strength of the screw 170 is weak, and the channel pipe sleeve 162 is deformed by a tightening load if the tightening strength is strong. Therefore, there is a problem that a desired inner diameter of the treatment instrument insertion channel 160 in the channel pipe sleeve 162 cannot be secured.

Therefore, as shown in FIG. 10, a configuration is made in which a width Nb of the flange 162f fitted in the screw hole 120h in the insertion direction N is wider than a conventional width Nc (Nb>Nc) and is wider than a distal end width Nd of the screw 170 (Nb>Nd>Nc).

According to such a configuration, since the load F' to the channel pipe sleeve 162 by tightening torque at the time of tightening the screw 170 is distributed on the flange 162f, deformation of the channel pipe sleeve 162 can be suppressed.

What is claimed is:

1. A laminated lens array comprising:
    a first lens having a first lens body, the first lens body having a first face and a second face opposing the first face over a first thickness of the first lens body in a first center axis direction, each of the first face and the second face being configured to at least indirectly receive incident light,
    wherein the first lens body has at least one first concavity formed on a first outer side surface of the first lens body, the at least one first concavity is curved inwardly toward a first center axis of the first lens body, the first outer side surface connecting the first face and the second face at an outer periphery of the first lens body; and
    a second lens provided one of proximally or distally to the first lens in the first center axis direction, and
    wherein the at least one first concavity is formed along an entirety of the first outer side surface in the first center axis direction.

2. The laminated lens array according to claim 1, wherein the second lens comprising:
    a second lens body having a third face and a fourth face opposing the third face over a second thickness of the second lens body in a second center axis direction;
    wherein the second lens body has at least one second concavity formed on a second outer side surface, the at least one second concavity is curved inwardly toward the second center axis of the second lens body.

3. The laminated lens array according to claim 2, further comprising:
    a third lens provided proximally relative to the second lens in a third center axis direction;
    wherein the third lens has a third lens body having a fifth face and a sixth face opposing the fifth face over a third thickness of the third lens body in the third center axis direction;
    the third lens body has at least one third concavity formed on a third outer side, the at least one third concavity is curved inwardly toward the third center axis of the third lens body.

4. The laminated lens array according to claim 2, wherein the second face is directly adhered to the third face.

5. The laminated lens array according to claim 2; wherein the at least one first concavity has a same radial position as the at least one second concavity.

6. An endoscope comprising:
    an insertion portion having an objective optical system at a distal end portion of the insertion portion; and
    the laminated lens array according to claim 1 disposed in the objective optical system.

7. The endoscope according to claim 6, wherein
    the distal end portion further comprises an image sensor;
    the image sensor is provided proximally relative to the laminated lens array, and the image sensor is configured to at least indirectly receive light through the laminated lens array; and
    the at least one concavity is located outside an effective field-of-view area of the image sensor.

8. An image pickup unit comprising:
    the laminated lens array according to claim 1; and
    an image sensor provided proximally relative to the laminated lens array, the image sensor configured to at least indirectly receive light through the laminated lens array.

9. The laminated lens array according to claim 1, wherein one or more of the first face and second face of the first lens body comprises a flat surface intersecting with the first center axis of the first lens body.

10. The laminated lens array according to claim 1, wherein the at least one first concavity is curved inwardly towards the first center axis such that a center of the at least one first concavity, in a circumferential direction, is closer to the first center axis than other portions of the at least one first concavity.

11. The laminated lens array according to claim 1, wherein the first lens and the second lens are objective lenses.

12. The laminated lens array according to claim 1, wherein the first lens and the second lens have a same cross-sectional shape orthogonal to the first center axis of the first lens body.

13. The laminated lens array according to claim 1, wherein the first outer side surface directly connects the first and second faces.

14. An endoscope comprising:
    an insertion portion having an objective optical system at a distal end portion of the insertion portion;
    a channel extending though the insertion portion and terminating at a distal end face of the distal end portion; and
    a laminated lens array disposed in the objective optical system, the laminated lens array comprising:
        a first lens having a first lens body, the first lens body having a first face and a second face opposing the first face over a first thickness of the first lens body in a first center axis direction, each of the first face and the second face being configured to at least indirectly receive incident light,
a second lens provided one of proximally or distally to the first lens in the first center axis direction; and
wherein the first lens body has at least one first concavity formed on a first outer side surface of the first lens body, the at least one first concavity is curved inwardly toward a first center axis of the first lens body, the first outer side surface connecting the first face and the second face at an outer periphery of the first lens body; and
a portion of the channel is disposed in at least a portion of the at least one first concavity.

\* \* \* \* \*